US008108482B2

United States Patent
Matsuoka et al.

(10) Patent No.: US 8,108,482 B2
(45) Date of Patent: Jan. 31, 2012

(54) DATA RELAYING APPARATUS, DATA RELAYING METHOD, AND DATA RELAY PROCESSING PROGRAM

(75) Inventors: Naoki Matsuoka, Kawasaki (JP); Tomohiro Ishihara, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 291 days.

(21) Appl. No.: 12/285,692

(22) Filed: Oct. 10, 2008

(65) Prior Publication Data

US 2009/0222533 A1    Sep. 3, 2009

(30) Foreign Application Priority Data

Feb. 29, 2008   (JP) ................................. 2008-050636

(51) Int. Cl.
*G06F 15/167* (2006.01)

(52) U.S. Cl. ........ 709/216; 709/203; 709/212; 709/217; 709/245; 707/706; 707/707; 707/708; 707/709; 707/710; 707/711; 707/712; 707/713; 707/722; 707/736

(58) Field of Classification Search .......... 707/706–713, 707/722, 736; 709/203, 216, 245, 212, 217
See application file for complete search history.

(56) References Cited

U.S. PATENT DOCUMENTS

| 6,571,248 | B1 * | 5/2003 | Kusama | 1/1 |
| 6,681,227 | B1 * | 1/2004 | Kojima et al. | 1/1 |
| 7,634,507 | B2 * | 12/2009 | Atluri et al. | 1/1 |
| 2002/0019977 | A1 * | 2/2002 | Matsuzuki | 717/170 |
| 2002/0107855 | A1 * | 8/2002 | Nishi | 707/9 |
| 2005/0004903 | A1 * | 1/2005 | Tsuda | 707/3 |
| 2007/0038950 | A1 * | 2/2007 | Taniguchi et al. | 715/768 |

FOREIGN PATENT DOCUMENTS

JP    2005-141507    6/2005

* cited by examiner

*Primary Examiner* — Michael Won
(74) *Attorney, Agent, or Firm* — Staas & Halsey LLP

(57) ABSTRACT

A data relaying apparatus disposed on the preceding stage of a registry server centrally managing meta-information extracts meta-information from a content retrieval result transmitted from the registry server to a client terminal and retains and correlates the meta-information with URI information included in the meta-information. On the other hand, a data relaying apparatus disposed on the preceding stage of a repository server retaining contents receives a content acquisition request transmitted from the client terminal to the repository server to extract URI information from the content acquisition request and transmits the URI information to the data relaying apparatus to acquire meta-information. The meta-information is added to contents transmitted to the client terminal before the contents are relayed.

17 Claims, 15 Drawing Sheets

FIG.3

```
HTTP/1.1 200 OK
Content - Type : text/xml; charset="utf - 8"
Date : Thu, 30 Aug 2007 04:54:44 GMT
Server : Apache - Coyote/1.1
Content - Length : 12776

:SOAP - ENV:Envelope xmlns:SOAP - ENV="http://schemas.xmlsoap.org/soap/envelope/">
:SOAP - ENV:Header>
:xdsheader SOAP - ENV:mustUnderstand= " 0 " ></xdsheader>
:/SOAP - ENV:Header>
:SOAP - ENV:Body>
<RegistryResponse status="Success" xmlns="urn:oasis:names:tc:ebxml - regrep:registry:xsd:2.1">
  <SQLQueryResult>
    <rim:ExtrinsicObject id="urn:uuid:b7ef187a  -5633 - 4af9 - a42c -ed95132713 8b" isOpaque="false" majorVersion="1" mimeType="text/xml" minorVersion="0"
      objectType="urn:uuid:7edca82f -054d - 47f2 - a032-  9b2a5b5186c1" status="Approved" xmlns:q="urn:oasis:names:tc:ebxml-regrep:query:xsd:2.1" xmlns:rim="urn:oasis:names:tc:ebxml- regrep:rim:xsd:2.1"> <AdhocQueryResponse xmlns="urn:oasis:names:tc:ebxml - regrep:query:xsd:2.1">
      <rim:Name>
        <rim:LocalizedString charset="UTF - 8" value="Physical" xml:lang="en - us"/>
      </rim:Name>
      <rim:Description/>
      <rim:Slot name=" FileName ">
        <rim:ValueList>
          <rim:Value> Karte_Taro Fuji </rim:Value>
        </rim:ValueList>
      </rim:Slot>
      <rim:Slot name=" URI">
        <rim:ValueList>
          <rim:Value> http://site-b.com/data/XXX.pdf </rim:Value>
        </rim:ValueList>
      </rim:Slot>
      <rim:Slot name=" SecurityLevel">
        <rim:ValueList>
          <rim:Value> 10 </rim:Value>
        </rim:ValueList>
      </rim:Slot>
      <rim:Slot name="applicationType">
        <rim:ValueList>
          <rim:Value> pdf </rim:Value>
        </rim:ValueList>
      </rim:Slot>
      <rim:Slot name=" Name ">
        <rim:ValueList>
          <rim:Value> Taro Fuji </rim:Value>
        </rim:ValueList>
      </rim:Slot>
      ……
  </SQLQueryResult>
</AdhocQueryResponse>
</RegistryResponse>
:/SOAP - ENV:Body>
:/SOAP - ENV:Envelope>
```

FIG.4

| URL INFORMATION | META INFORMATION |
|---|---|
| http://site-b.com/data/XXX.pdf | <FileName>Karte_Taro Fuji</FileName> |
| | <SecurityLevel>10</SecurityLevel> |
| | <applicationType>pdf<applicationType> |
| | <Name>Taro Fuji</Name> |
| | ⋮ |
| http://site-b.com/ref/YYY.jpg | <FileName>Karte_Taro Fuji</FileName> |
| | <SecurityLevel>3</SecurityLevel> |
| | <applicationType>jpg<applicationType> |
| | <Name>Taro Fuji</Name> |
| | ⋮ |
| ⋮ | ⋮ |

FIG.5

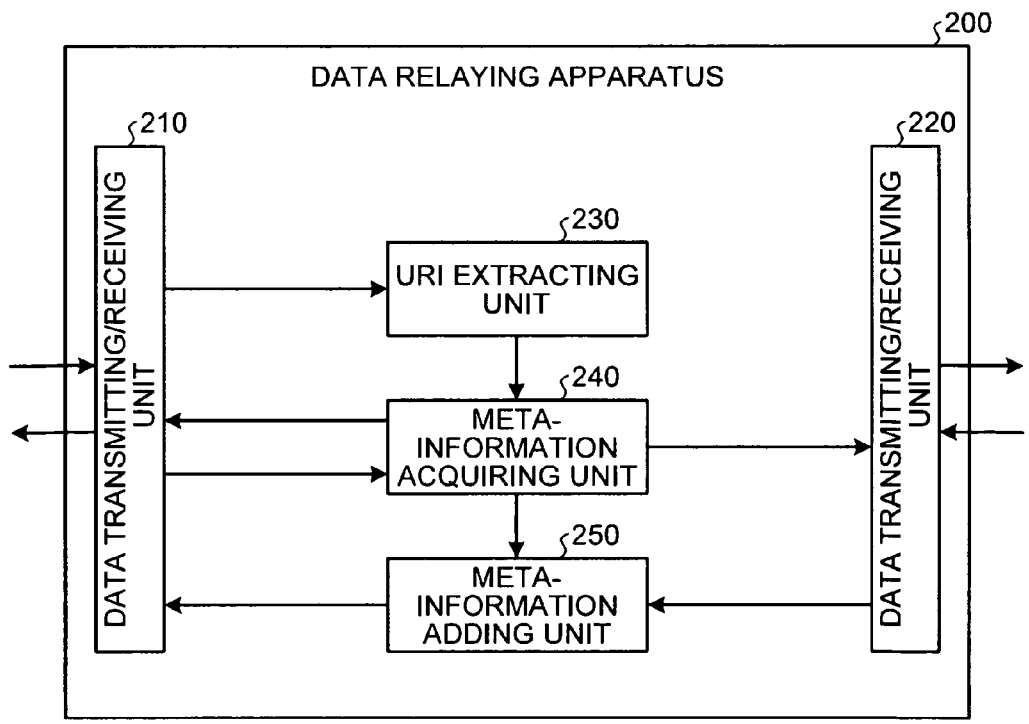

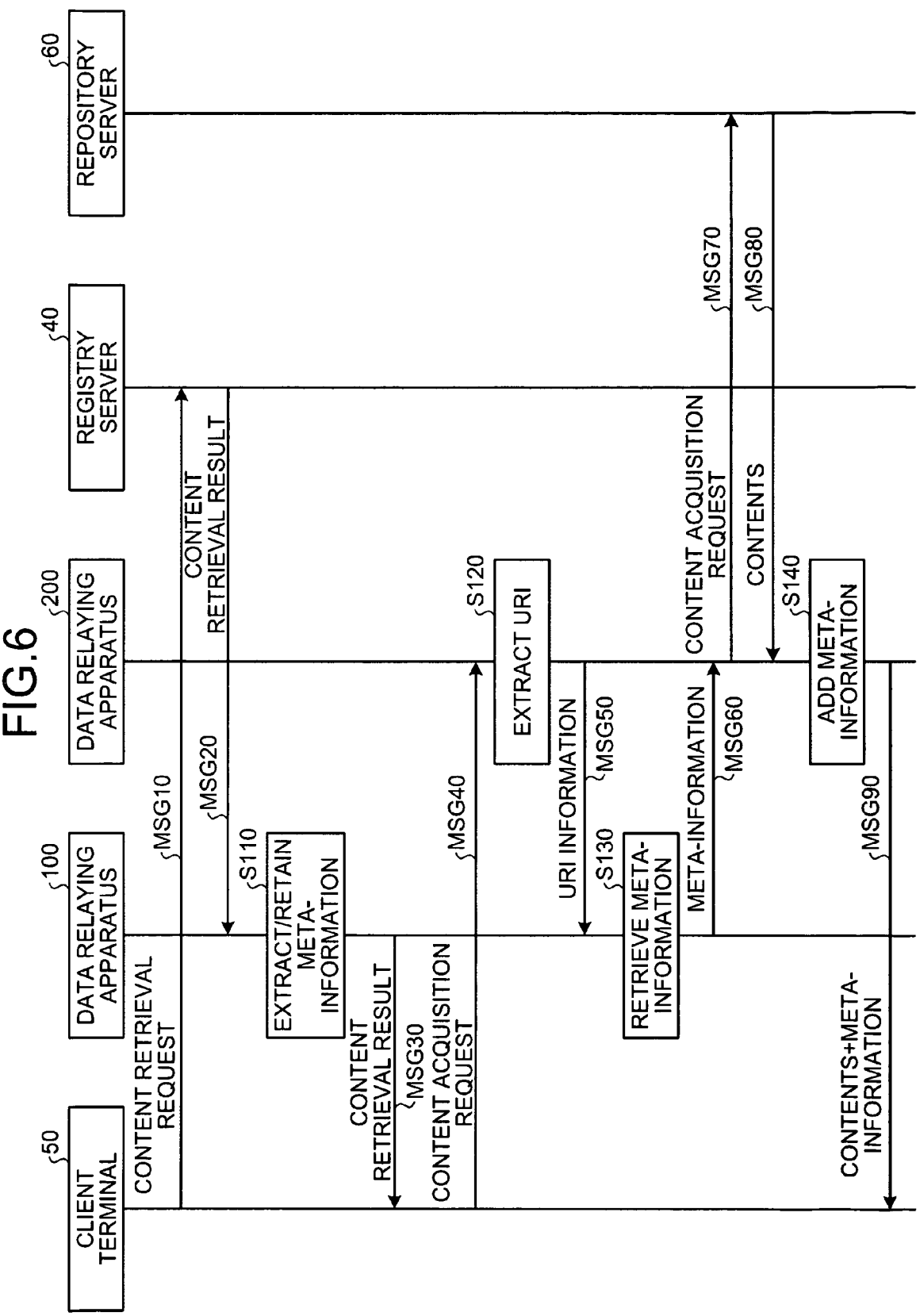

DATA RELAYING APPARATUS, DATA RELAYING METHOD, AND DATA RELAY PROCESSING PROGRAM

BACKGROUND OF THE INVENTION

1. Field of the Invention

The present invention relates to a data relaying apparatus disposed in a network including meta-information and contents independently managed, a data relaying method in the data relaying apparatus, and a data relay processing program executed by a computer that is the data relaying apparatus.

2. Description of the Related Art

Conventionally, contents such as document data, video data, and music data are transmitted and received over a network.

Important contents among these contents may strongly require management of distribution situations. In such a case, for example, as shown in FIG. 15, computers and data relaying apparatuses 702 on the server side and the client side are provided with a log function.

A distribution situation managing apparatus 703 collects and integrally manages logs for applications recorded in computers 701 and logs of the network layer (transmission sources, destinations, access times, etc.) recorded in the data relaying apparatuses 702. This enables management of distribution situations of contents.

For example, as shown in FIG. 16, if contents are transmitted from a content server 704 to a client terminal 705, data relaying apparatuses 706 relaying the contents extract meta-information added to the contents to correlate and store the meta-information with the log of the network layer.

The distribution situation managing apparatus 703 collects and manages information stored in the data relaying apparatuses 706. This enables management of distribution situations of contents.

By the way, the management of communication record shown in FIG. 15 is smoothly performed on the premise that the computers 701 on the server side and the client side are suitably operated/managed and that the computers certainly record the log.

Therefore, a system administrator or a user with IT skills suitably operating/managing the computers is absolutely necessary.

However, few employees have sufficient IT skills in the case of small clinics and offices and computers are not necessarily operated/managed suitably in many cases.

In such a case, communication records may not certainly be collected by the computers due to infection with a computer virus, a failure of computers, etc., and it is problematic that the credibility of the communication records deteriorates in a field requiring strict communication records.

If computers collect logs, the communication records are at risk of being altered by end users since the logs may easily be altered.

It is problematic that communication records of computers without the log function may not be managed.

Therefore, when communication records are managed, the method of using meta-information of FIG. 16 is more desirable than the method shown in FIG. 15.

Contents are generally given meta-information and many systems utilize the meta-information (e.g., Japanese Patent Application Laid-open Publication No. 2005-141507). Therefore, it is conceivable that the management of communication records with the above method is easily introduced into such systems.

Recently, XDS (Cross-enterprise Document Sharing) is planned in medical institutions handling medical care information (electronic medical charts and medical images of patients), which is a highly important content.

The XDS enables continuous utilization of medical care information of patients with medical care information and meta-information stored in separate servers instead of storing medical care information along with meta-information in a server.

Specifically explaining with reference to FIG. 17, first, it is assumed that medical care information of a patient is created in a medical institution "B".

The medical care information is stored in a repository server 707 in the medical institution "B", and meta-information of the medical care information is stored in a registry server 708 in a registry institution.

When the same patient receives medical care from a medical institution "A", a client terminal 709 in the medical institution "A" requests the registry server 708 to retrieve the medical care information of the patient.

The requested registry server 708 retrieves corresponding meta-information from the stored meta-information with the use of a patient ID, etc.

As a result of the retrieval, the registry server 708 transmits information indicating the location of medical care information (such as URI (Uniform Resource Identifier)) included in the meta-information to the client terminal 709.

The client terminal 709 receives the information indicating the location and acquires target medical care information from the repository server 707 in the medical institution "B" indicated by the information.

This provides a system enabling continuous utilization of medical care information of patients without the need for creating new medical care information if a patient receives medical care from a medical institute different from the previous one.

Since the medical care information includes not only personal information but also information not desired to be known to others, strict control is strongly required for the management of distribution situations of medical care information when XDS is implemented.

That is, it is desirable to certainly manage when, by whom, from where to where, and what information is utilized to put restrictions on unauthorized takeout, etc., of medical care information.

Since the meta-information stored in the registry server 708 includes a file name, a patient name, age, etc., it is desirable to store meta-information of medical care information and the log of the network layer into a data relaying apparatus relaying the medical care information when medical care information is acquired from the repository server 707. As a result, management may certainly be performed for when, by whom, from where to where, and what information is utilized.

However, since the meta-information and the medical care information are separately stored and the repository server 707 transmits only the medical care information to the client terminal 709, it is difficult to manage distribution situations with the use of the meta-information as shown in FIG. 16.

It is problematic that the strict management of distribution situations of contents is difficult in an environment with meta-information and contents separately managed as represented by XDS.

SUMMARY

It is an object of the present invention to at least partially solve the problems in the conventional technology.

According to an aspect of the present invention, a data relaying apparatus disposed on a network with contents and meta-information managed separately in different servers includes a meta-information extracting unit extracts meta-information from a content retrieval result, the content retrieval result being transmitted to a client terminal from a registry server accepting a content retrieval request from the client terminal, the registry server centrally managing the meta-information; a meta-information registering unit that registers the meta-information extracted by the meta-information extracting unit into a meta-information storage unit in correlation with location information included in the meta-information, the location information uniquely defining a location of contents; and a meta-information transmitting unit that externally receives a meta-information acquisition request with the location information specified to retrieve meta-information correlated with the location information from the meta-information storage unit, the meta-information transmitting unit transmitting the meta-information acquired as a result of the retrieval to a request source.

According to another aspect of the present invention, a data relaying apparatus disposed on a network with contents and meta-information managed separately in different servers includes a location information extracting unit that extracts location information uniquely defining a location of contents from a content acquisition request, the content acquisition request being transmitted from a client terminal to a repository server retaining the contents; a meta-information acquiring unit that transmits a meta-information acquisition request to a data relaying apparatus cooperating with a registry server managing the meta-information with the use of the location information extracted by the location information extracting unit to acquire meta-information; and a content transmitting unit that receives contents to add the meta-information acquired by the meta-information acquiring unit to the contents, the contents being transmitted by the repository server accepting the content acquisition request to the client terminal transmitting the content acquisition request, the content transmitting unit relaying the contents to the client terminal.

According to still another aspect of the present invention, a data relaying apparatus disposed on a network with contents and meta-information managed separately in different servers includes a meta-information extracting unit that extracts meta-information from a content retrieval result, the content retrieval result being transmitted to a client terminal from a registry server accepting a content retrieval request from the client terminal, the registry server managing the meta-information; and a meta-information transmitting unit that transmits the meta-information extracted by the meta-information extracting unit to a destination determined by location information included in the meta-information, the location information uniquely defining a location of contents.

According to still another aspect of the present invention, a data relaying apparatus disposed on a network with contents and meta-information managed separately in different servers includes a meta-information registering unit that registers meta-information into a meta-information storage unit in correlation with location information included in the meta-information, the location information uniquely defining a location of contents, the meta-information being received from a data relaying apparatus cooperating with a registry server managing the meta-information; a location information extracting unit that extracts the location information from the content acquisition request, the content acquisition request being transmitted from a client terminal to a repository server retaining the contents; a meta information acquiring unit that acquires meta-information correlated with the location information extracted by the location information extracting unit from the meta-information storage unit; and a content relaying unit that receives contents to add the meta-information acquired by the meta-information acquiring unit to the contents, the contents being transmitted by the repository server accepting the content acquisition request to the client terminal transmitting the content acquisition request, the content relaying unit relaying the contents to the client terminal.

According to still another aspect of the present invention, a data relaying apparatus disposed on a network with contents and meta-information managed separately in different servers includes a meta-information extracting unit that extracts meta-information from a content retrieval result, the content retrieval result being transmitted to a client terminal from a registry server accepting a content retrieval request from the client terminal, the registry server centrally managing the meta-information; a meta-information registering unit that registers the meta-information extracted by the meta-information extracting unit into a meta-information storage unit in correlation with location information included in the meta-information, the location information uniquely defining a location of contents; a location information extracting unit that receives a content acquisition request to extract the location information from the content acquisition request, the content acquisition request being transmitted to a repository server retaining the contents; a meta information acquiring unit that acquires meta-information correlated with the location information extracted by the location information extracting unit from the meta-information storage unit; and a content transmitting unit that receives contents to add the meta-information acquired by the meta-information acquiring unit to the contents, the contents being transmitted by the repository server accepting the content acquisition request to the client terminal transmitting the content acquisition request, the content transmitting unit relaying the contents to the client terminal.

According to still another aspect of the present invention, a method for relaying data in a network with contents and meta-information managed separately in different servers includes extracting meta-information from a received content retrieval result transmitted to a client terminal from a registry server accepting a content retrieval request from the client terminal, the registry server centrally managing the meta-information; registering the extracted meta-information into a storage unit in correlation with location information included in the meta-information, the location information uniquely defining a location of contents; and retrieving meta-information correlated with location information from the storage unit, the location information being specified in an externally-received meta-information acquisition request retrieve to transmit the meta-information acquired as a result of the retrieval to a request source.

According to still another aspect of the present invention, a method for relaying data in a network with contents and meta-information managed separately in different servers includes extracting location information uniquely defining a location of contents from a received content acquisition request transmitted from a client terminal to a repository server retaining the contents; acquiring meta information by transmitting a meta-information acquisition request to a data relaying apparatus cooperating with a registry server managing the meta-information with the use of the extracted location information; and adding the acquired meta-information to contents, the contents being transmitted from the repository server accepting the content acquisition request to the client terminal transmitting the content acquisition request; and relaying the contents with the meta-information to the client terminal.

According to still another aspect of the present invention, a method for relaying data in a network with contents and meta-information managed separately in different servers includes extracting meta-information from a received content retrieval result transmitted to a client terminal from a registry server accepting a content retrieval request from the client terminal, the registry server managing the meta-information; and transmitting the extracted meta-information to a destination determined by location information included in the meta-information, the location information uniquely defining a location of contents.

According to still another aspect of the present invention, a method for relaying data in a network with contents and meta-information managed separately in different servers includes registering meta-information into a storage unit in correlation with location information included in the meta-information, the meta-information being received from a data relaying apparatus cooperating with a registry server managing the meta-information, the location information uniquely defining a location of contents; extracting the location information from the content acquisition request, the content acquisition request being transmitted from a client terminal to a repository server retaining the contents; acquiring meta-information correlated with the extracted location information from the storage unit; adding the acquired meta-information to contents, the contents being transmitted from the repository server accepting the content acquisition request to the client terminal transmitting the content acquisition request; and relaying the contents with the meta-information to the client terminal.

According to still another aspect of the present invention, a method for relaying data in a network with contents and meta-information managed separately in different servers includes extracting meta-information from a content retrieval result, the content retrieval result being transmitted to a client terminal from a registry server accepting a content retrieval request from the client terminal, the registry server centrally managing the meta-information; registering the extracted meta-information into a storage unit in correlation with location information included in the meta-information, the location information uniquely defining a location of contents; extracting the location information from a content acquisition request transmitted to a repository server retaining the contents; acquiring meta-information correlated with the extracted location information from the storage unit; adding the acquired meta-information to the contents, the contents being transmitted from the repository server accepting the content acquisition request to the client terminal transmitting the content acquisition request; and relaying the contents with the meta-information to the client terminal.

According to still another aspect of the present invention, a computer program product causes a computer to perform the method according to the present invention.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a view of an example of information of a content search result;

FIG. 4 is a view of an example of information stored in a meta-information storage unit 140;

FIG. 5 is a block diagram of a schematic configuration of a data relaying apparatus 200;

FIG. 6 is a sequence view of a schematic of a process in apparatuses of the first embodiment;

DETAILED DESCRIPTION OF THE PREFERRED EMBODIMENTS

Exemplary embodiments of a data relaying apparatus, a data relaying method, and a data relay processing program will be explained in detail with reference to the accompanying drawings.

Figure 1:
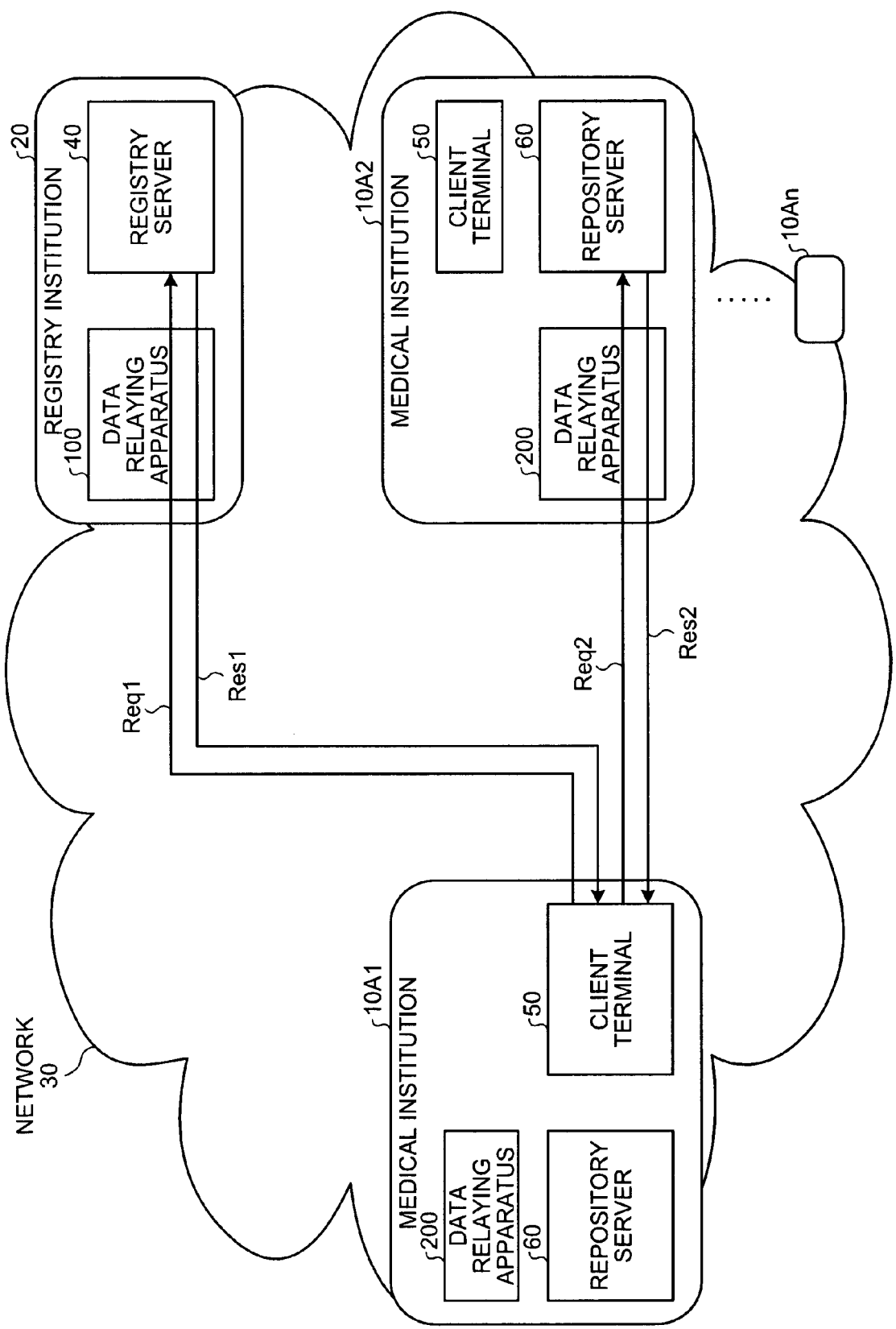
FIG. 1 is an explanatory view of a schematic of a medical network disposed with a data relaying apparatus according to a first embodiment.

A schematic of a medical network disposed with a data relaying apparatus according to a first embodiment will be explained with reference to FIG. 1. As shown in FIG. 1, computer networks (LAN and WAN) are established in each institution of medical institutions 10A1 to 10An and registry institution 20, and the institutions are communicably connected to each other through a network 30 (public telephone network and Internet). XDS explained later is implemented in such a medical network.

That is, the registry institution 20 is disposed with a registry server 40, and the registry server 40 retains meta-information about contents (electronic medical charts and medical images of patients) and returns a content retrieval result (Res1) including the meta-information in response to a content retrieval request (Req1) from the medical institutions 10A1 to 10An.

The medical institutions 10A1 to 10An are disposed with client terminals 50 and repository servers 60.

For example, the client terminal 50 of the medical institution 10A1 transmits the content retrieval request (Req1) to the registry server 40 in accordance with user's operation.

Since the content retrieval result is returned from the registry server 40, a user determines which medical institution the user acquires contents from depending on the content retrieval result.

The client terminal 50 transmits the content acquisition request (Req2) to the repository server 60 of the medical institution 10A2 in accordance with user's operation.

The repository server 60 retains contents and transmits the corresponding contents to the client terminal 50 (Res2) in accordance with the content acquisition request (Req2) from the client terminal 50.

The data relaying apparatus of the first embodiment corresponds to the data relaying apparatus 100 disposed on the preceding stage of the registry server 40 (at a position relaying data transmitted/received by the registry server 40 and the client terminal 50) and the data relaying apparatus 200 disposed on the preceding stage of the repository server 60 (at a position relaying data transmitted/received by the repository server 60 and the client terminal 50 of another medical institution) in such a medical network.

Figure 2:
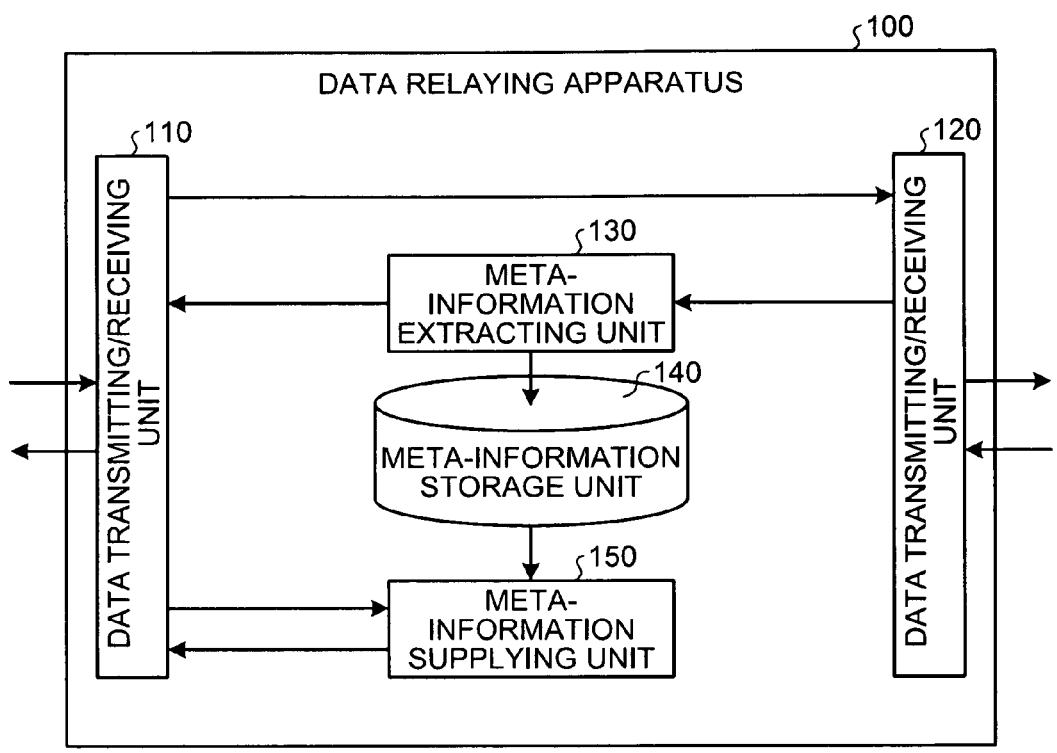
FIG. 2 is a block diagram of a schematic configuration of a data relaying apparatus 100.

A schematic configuration of the data relaying apparatus 100 will be explained with reference to FIG. 2. As shown in FIG. 2, the data relaying apparatus 100 includes data transmitting/receiving units 110 to 120, a meta-information extracting unit 130, the meta-information storage unit 140, and a meta-information supplying unit 150.

The data transmitting/receiving unit 110 executes transmission/reception processes of data for the medical institutions 10A1 to 10An. The data transmitting/receiving unit 120 executes transmission/reception processes of data for the registry server 40. The data transmitting/receiving unit 110 determines a type of a received message and determines an output destination depending on the determination result.

The meta-information extracting unit 130 extracts meta-information from the content retrieval result transmitted from the registry server 40 to the client terminals 50 and registers and correlates the meta-information with location information uniquely defining the location of the contents into the meta-information storage unit 140.

Specifically, the meta-information extracting unit 130 receives the content retrieval result transmitted by the registry server 40 from the data transmitting/receiving unit 120.

The content retrieval result is transmitted as a packet and the meta-information extracting unit 130 performs snooping of the packet received from the data transmitting/receiving unit 120 to extract the meta-information.

FIG. 3 is a view of an example of information of the content retrieval result, and the meta-information extracting unit 130 extracts meta-information such as "File Name" and "Karte_Taro Fuji" as shown in FIG. 3.

The meta-information extracting unit 130 uses URI (Uniform Resource Identifier), which is a unique identifier included in the meta-information, as an entry key to register and correlate the meta-information with the URI information into the meta-information storage unit 140.

After the registration, the meta-information extracting unit 130 outputs the content retrieval result to the data transmitting/receiving unit 110.

The meta-information storage unit 140 accepts the registration to have the meta-information stored thereon. Specifically, as shown in FIG. 4, the meta-information storage unit 140 has stored thereon the meta-information (such as <FileName>Karte_Taro Fuji</FileName>) correlated with the URI information (http://site-b.com/data/XXX.pdf).

When URI information is received from the outside, the meta-information supplying unit 150 retrieves meta-information correlated with the URI information from the meta-information storage unit 140 and transmits the meta-information to the transmission source of the URI information.

Specifically, the meta-information supplying unit 150 receives the URI information transmitted by the data relaying apparatus 200 from the data transmitting/receiving unit 110.

The meta-information supplying unit 150 uses the URI information as a search key to search the meta-information storage unit 140 to acquire meta-information correlated with the URI information. The meta-information supplying unit 150 outputs the acquired meta-information to the data transmitting/receiving unit 110 with a destination set as the data relaying apparatus 200.

A schematic configuration of the data relaying apparatus 200 will be explained with reference to FIG. 5. As shown in FIG. 5, the data relaying apparatus 200 includes data transmitting/receiving units 210 to 220, a URI extracting unit 230, a meta-information acquiring unit 240, and a meta-information adding unit 250.

The data transmitting/receiving unit 210 executes transmission/reception processes of data for other medical institutions or the registry institution 20. The data transmitting/receiving unit 220 executes transmission/reception processes of data for the repository server 60. The data transmitting/receiving unit 210 determines a type of a received message and determines an output destination depending on the determination result.

When receiving a content acquisition request transmitted to the repository server 60 from the client terminal 50, the URI extracting unit 230 extracts the URI information from the content acquisition request.

Specifically, the URI extracting unit 230 receives the content acquisition request from the data transmitting/receiving unit 210, extracts the URI information from the content acquisition request, and outputs the URI information and the content acquisition request to the meta-information acquiring unit 240.

The meta-information acquiring unit 240 transmits the URI information extracted by the URI extracting unit 230 to a predetermined communicating apparatus to acquire meta-information.

Specifically, the meta-information acquiring unit 240 receives the URI information and the content acquisition request from the URI extracting unit 230 and outputs the URI information destined for the data relaying apparatus 100 to the data transmitting/receiving unit 210.

The meta-information acquiring unit 240 subsequently receives the meta-information from the data transmitting/receiving unit 210, outputs the meta-information to the meta-information adding unit 250, and outputs the content acquisition request to the data transmitting/receiving unit 220.

The meta-information adding unit 250 receives the contents transmitted to the client terminal 50 from the repository server 60, adds the meta-information acquired by the meta-information acquiring unit 240 to the contents, and relays the contents to the client terminal 50.

Specifically, the meta-information adding unit 250 receives contents from the data transmitting/receiving unit 220, adds the meta-information received earlier from the meta-information acquiring unit 240 to the contents, and outputs the contents to the data transmitting/receiving unit 210.

A method of adding meta-information to contents may be, for example, directly writing into content data, adding as appended information of content data, or adding to a packet header or protocol header portion used for the content transfer.

A process flow of the apparatuses will lastly be explained with reference to FIG. 6. The client terminal 50 first transmits a content retrieval request to the registry server 40 (MSG10).

The registry server 40 receives the content retrieval request through the data relaying apparatus 100 and transmits a content retrieval result to the client terminal 50 (MSG20).

When relaying the content retrieval result to the client terminal 50 (MSG30), the data relaying apparatus 100 extracts, correlates, and retains meta-information with URI information (Step S110).

The client terminal 50 receives the content retrieval result through the data relaying apparatus 100 and transmits a content acquisition request to the repository server 60 (MSG40).

Before relating the content acquisition request to the repository server 60, the data relaying apparatus 200 extracts URI information (Step S120) and transmits the URI information to the data relaying apparatus 100 (MSG50).

The data relaying apparatus 100 receives the URI information from the data relaying apparatus 200 and retrieves meta-information correlated with the URI information among the retained meta-information (Step S130).

The data relaying apparatus 100 transmits the meta-information acquired as a result of the retrieval to the data relaying apparatus 200 (MSG60).

The data relaying apparatus 200 receives the meta-information from the data relaying apparatus 100 and relays the content acquisition request to the repository server 60 (MSG70).

The repository server 60 receives the content acquisition request through the data relaying apparatus 200 and transmits contents to the client terminal 50 (MSG80).

The data relaying apparatus 200 adds the meta-information received from the data relaying apparatus 200 to the contents (Step S140) and relays the contents to the client terminal 50 (MSG 90).

As explained above, when relaying the contents from the repository server 60 to the client terminal 50, the data relaying apparatus 200 finally adds the meta-information to the contents before relaying the contents.

Therefore, even if the meta-information and the contents are separately stored as in the case of the medical network of FIG. 1, when the data relaying apparatus 200 relays the contents, the control of distribution situations of contents may strictly be performed by recording meta-information added to the contents and communication information related to the relay (destination of the contents (IP address)).

Since it is not required to collect logs from the client terminals and the servers, unavailability of logs is not caused due to a failure of the apparatuses and a risk of alteration of logs is not posed.

Since the existing data relaying apparatuses may be driven to execute the above processes, a client terminal or a special function of the servers may not newly be added to manage the distribution situations of contents.

The distribution situations of contents may centrally be managed by collecting and managing the information stored in the data relaying apparatuses of the medical institutions.

In the first embodiment, when the data relaying apparatus 100 disposed on the preceding stage of the registry server 40 accepts a meta-information acquisition request from the data relaying apparatus 200 disposed on the preceding stage of the repository server 60, the data relaying apparatus 100 supplies the meta-information to the data relaying apparatus 200.

In a data relaying apparatus according to a second embodiment, the meta-information is supplied at a timing different from the first embodiment, and the data relaying apparatus 300 corresponding to the data relaying apparatus 100 supplies the meta-information to the data relaying apparatus 400 corresponding to the data relaying apparatus 200 when the meta-information is extracted from the content retrieval result.

Figure 7:
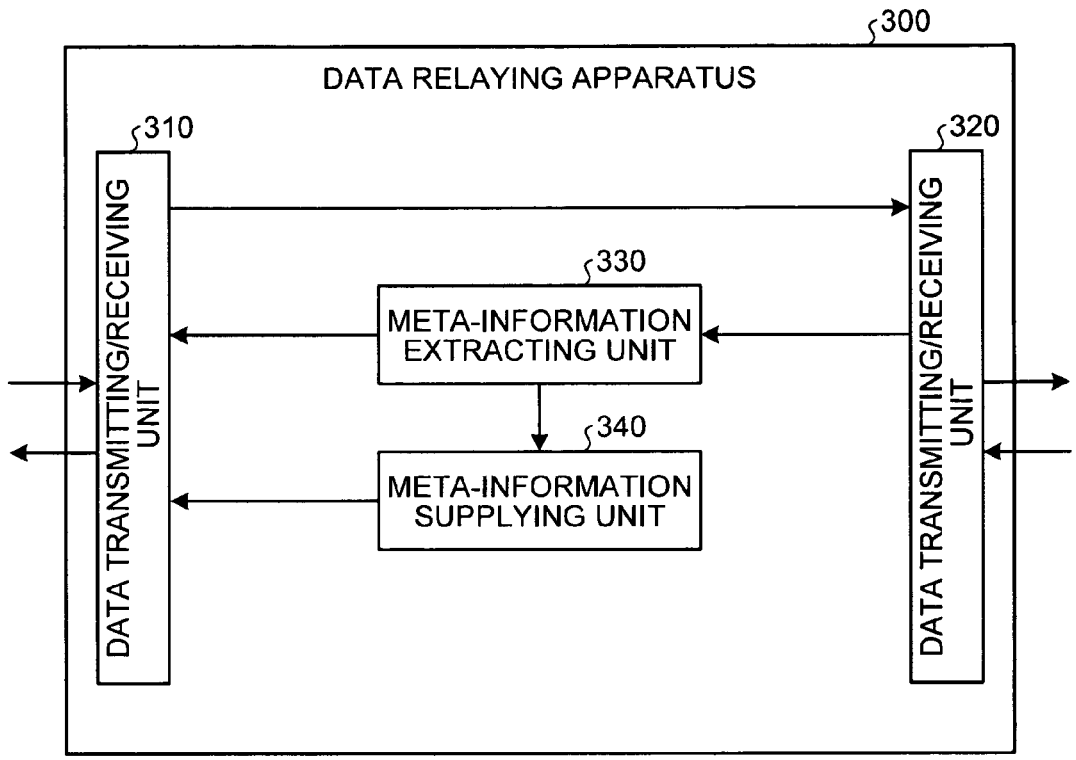
FIG. 7 is a block diagram of a schematic configuration of a data relaying apparatus 300.

A schematic configuration of the data relaying apparatus 300 will be explained with reference to FIG. 7. As shown in FIG. 7, the data relaying apparatus 300 includes data transmitting/receiving units 310 to 320, a meta-information extracting unit 330, and a meta-information supplying unit 340.

The data transmitting/receiving unit 310 executes transmission/reception processes of data for the medical institutions 10A1 to 10An. The data transmitting/receiving unit 320 executes transmission/reception processes of data for the registry server 40.

When the registry server 40 accepts a content retrieval request from the arbitrary client terminal 50 and transmits a content retrieval result to the client terminal 50, the meta-information extracting unit 330 receives the content retrieval result and extracts meta-information from the content retrieval result.

Specifically, the meta-information extracting unit 330 receives the content retrieval result from the data transmitting/receiving unit 320 and extracts meta-information from the content retrieval result. The meta-information extracting unit 330 outputs the extracted meta-information to the meta-information supplying unit 340 and outputs the content retrieval result to the data transmitting/receiving unit 310.

The meta-information supplying unit 340 transmits the meta-information to a destination determined by URI information included in the meta-information extracted by the meta-information extracting unit 330.

Specifically, the meta-information supplying unit 340 receives the meta-information from the meta-information extracting unit 330 and determines a destination from the URI information included in the meta-information.

For example, the meta-information supplying unit 340 receives three pieces of meta-information, which are meta-information for contents "X", meta-information for contents "Y", and meta-information for contents "Z" from the meta-information extracting unit 330.

If pieces of URI information included in the meta-information are "http://site-b.com/data/XXX.pdf", "http://site-c.com/ref/YYY.pdf", and "http://site-d.com/file/ZZZ.pdf", the meta-information supplying unit 340 determines that the meta-information for contents "X" is destined for site-b.com, that the meta-information for contents "Y" is destined for site-c.com, and that the meta-information for contents "Z" is destined for site-d.com. The meta-information supplying unit 340 transmits the pieces of the meta-information to the determined destinations.

Site-c.com, etc., are addresses in the FQDN notation, and the meta-information is actually transmitted to IP addresses corresponding to site-c.com, etc., with the use of DNS. When the meta-information supplying unit 340 transmits meta-information, a special port number may be used.

Figure 8:
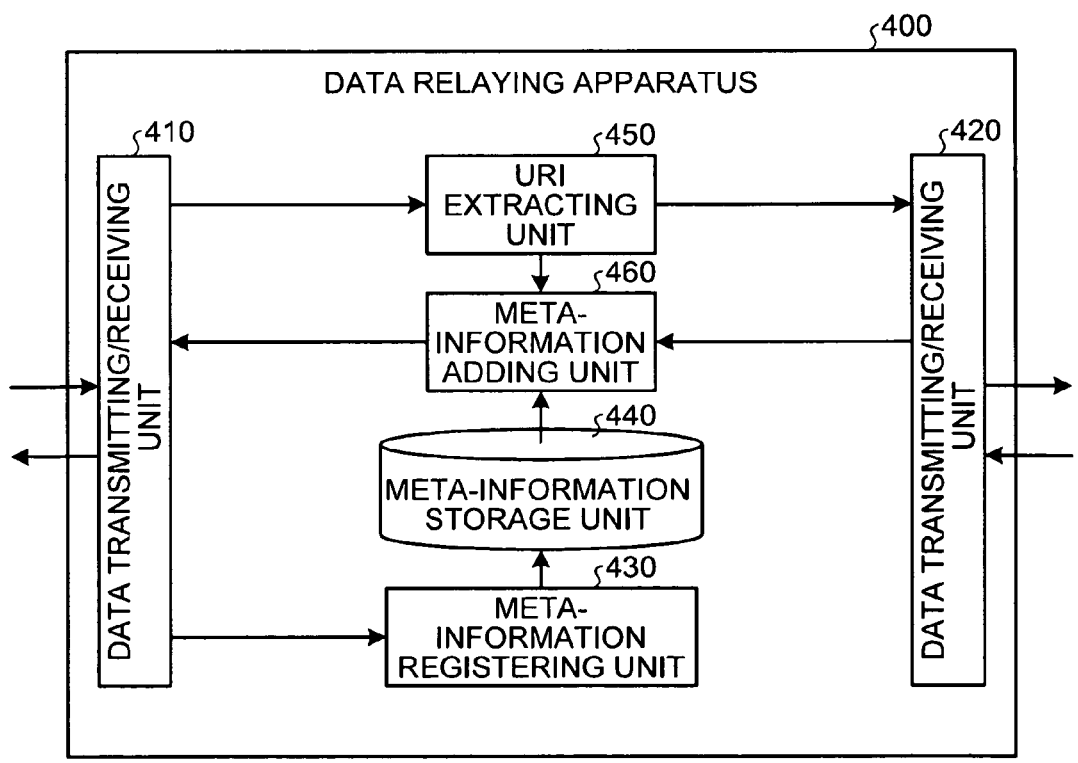
FIG. 8 is a block diagram of a schematic configuration of a data relaying apparatus 400.

A schematic configuration of the data relaying apparatus 400 will be explained with reference to FIG. 8. As shown in FIG. 8, the data relaying apparatus 400 includes data transmitting/receiving units 410 to 420, a meta-information registering unit 430, a meta-information storage unit 440, a URI extracting unit 450, and a meta-information adding unit 460.

The data transmitting/receiving unit 410 executes transmission/reception processes of data for other medical institutions or the registry institution 20. The data transmitting/receiving unit 420 executes transmission/reception processes of data for the repository server 60.

When arbitrary meta-information is received from the data relaying apparatus 300, the meta-information registering unit 430 registers and correlates the meta-information with URI information included in the meta-information into the meta-information storage unit 440.

Specifically, the meta-information registering unit 430 receives the meta-information from the data transmitting/receiving unit 410 and uses the URI information included in the meta-information as an entry key to register and correlate the meta-information with the URI information into the meta-information storage unit 440.

The meta-information storage unit 440 accepts the registration to have the meta-information stored thereon. A specific example is as shown in FIG. 4 and will not be explained.

The URI extracting unit 450 receives a content acquisition request transmitted to the repository server 60 from the client terminal 50 and extracts the URI information from the content acquisition request.

Specifically, the URI extracting unit 450 receives the content acquisition request from the data transmitting/receiving unit 410, extracts the URI information, outputs the URI information to the meta-information adding unit 460, and outputs the content acquisition request to the data transmitting/receiving unit 420.

When relaying the contents transmitted by the repository server 60 to the client terminal 50, the meta-information adding unit 460 retrieves meta-information correlated with the URI information extracted by the URI extracting unit 450 from the meta-information storage unit 440, adds the meta-information acquired as a result of the retrieval to the contents, and relays the contents to the client terminal 50.

Specifically, since the meta-information adding unit 460 first receives the URI information from the URI extracting unit 450, the meta-information adding unit 460 acquires meta-information correlated to the URI information from the meta-information storage unit 440. The meta-information adding unit 460 subsequently receives contents from the data transmitting/receiving unit 420, adds the meta-information received earlier to the contents, and outputs the contents to the data transmitting/receiving unit 410.

Figure 9:
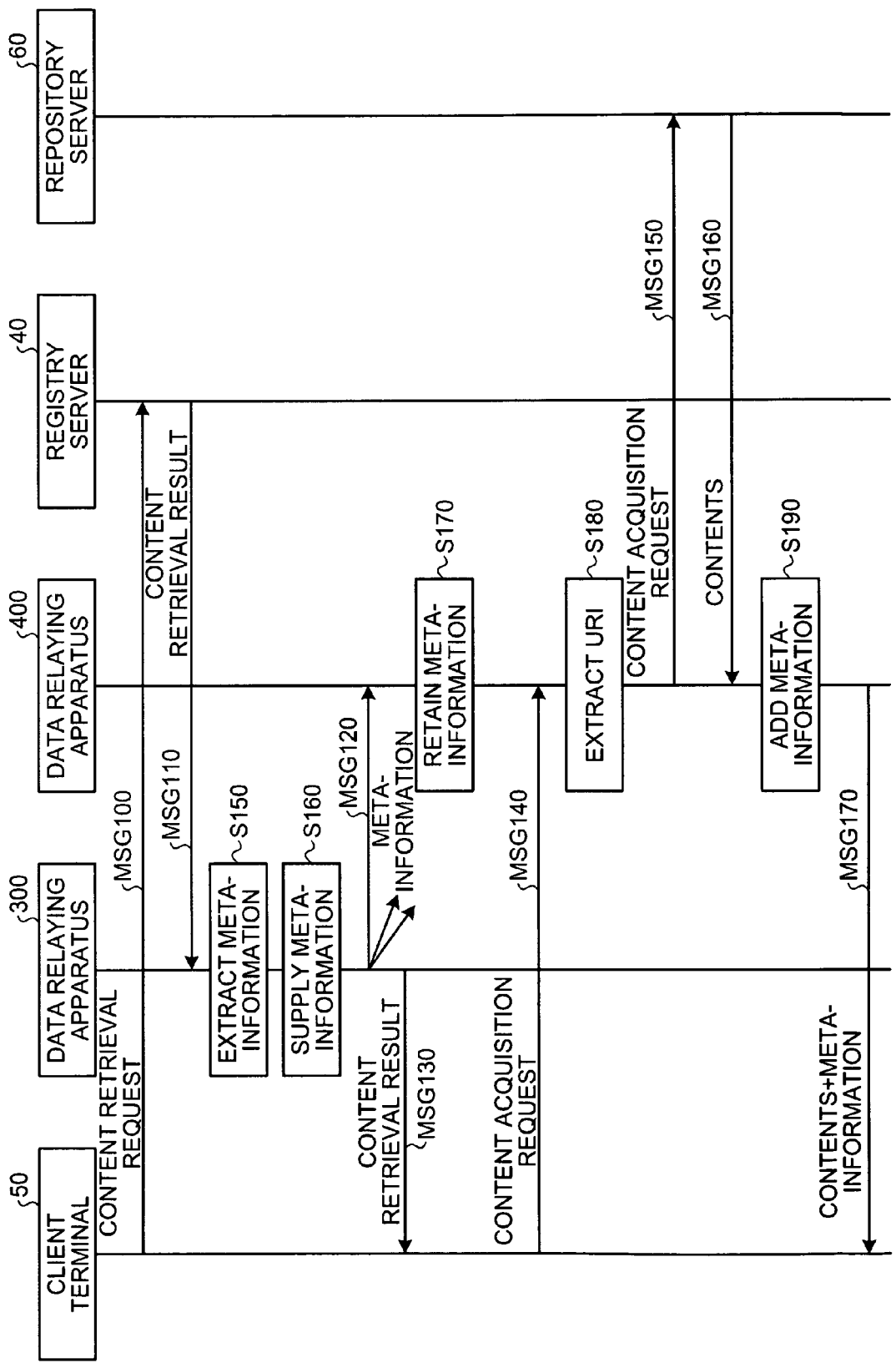
FIG. 9 is a sequence view of a schematic of a process in apparatuses of a second embodiment.

A process flow of the apparatuses will then be explained with reference to FIG. 9. The client terminal 50 first transmits a content retrieval request to the registry server 40 (MSG100).

The registry server 40 receives the content retrieval request through the data relaying apparatus 300 and transmits a content retrieval result to the client terminal 50 (MSG110).

The data relaying apparatus 300 receives the content retrieval result from the registry server 40, extracts meta-information (Step S150), and supplies the meta-information to a destination determined by URI information (Step S160). This causes the meta-information to be transmitted to the data relaying apparatus 400 (MSG120), for example, and the data relaying apparatus 400 retains and correlates the meta-information with the URI information (Step S170).

The data relaying apparatus 300 transfers the content retrieval result to the client terminal 50 (MSG130).

The client terminal 50 receives the content retrieval result through the data relaying apparatus 300 and transmits a content acquisition request to the repository server 60 (MSG140).

The data relaying apparatus 400 extracts the URI information from the content acquisition request (Step S180) and acquires the meta-information correlated to the URI information from the meta-information storage unit 440.

The data relaying apparatus 400 relays the content acquisition request to the repository server 60 (MSG150).

The repository server 60 receives the content acquisition request through the data relaying apparatus 400 and transmits contents to the client terminal 50 (MSG160).

The data relaying apparatus 400 receives the contents from the repository server 60, adds the meta-information received earlier (Step S190), and relays the contents to the client terminal 50 (MSG170).

As explained above, meta-information is delivered to the data relaying apparatus 400 disposed on the preceding stages of the repository servers 60 when the meta-information is extracted in the second embodiment. This enables the data relaying apparatus 400 to immediately acquire the meta-information from the own apparatus instead of acquiring the meta-information from the data relaying apparatus disposed on the preceding stage of the registry server 40 and, therefore, this enables high-speed content transfer to the client terminal.

Although the first and second embodiments are directed to a plurality of data relaying apparatuses disposed on respective institutions, a third embodiment explained below is directed to one data relaying apparatus disposed on a network.

Figure 10:
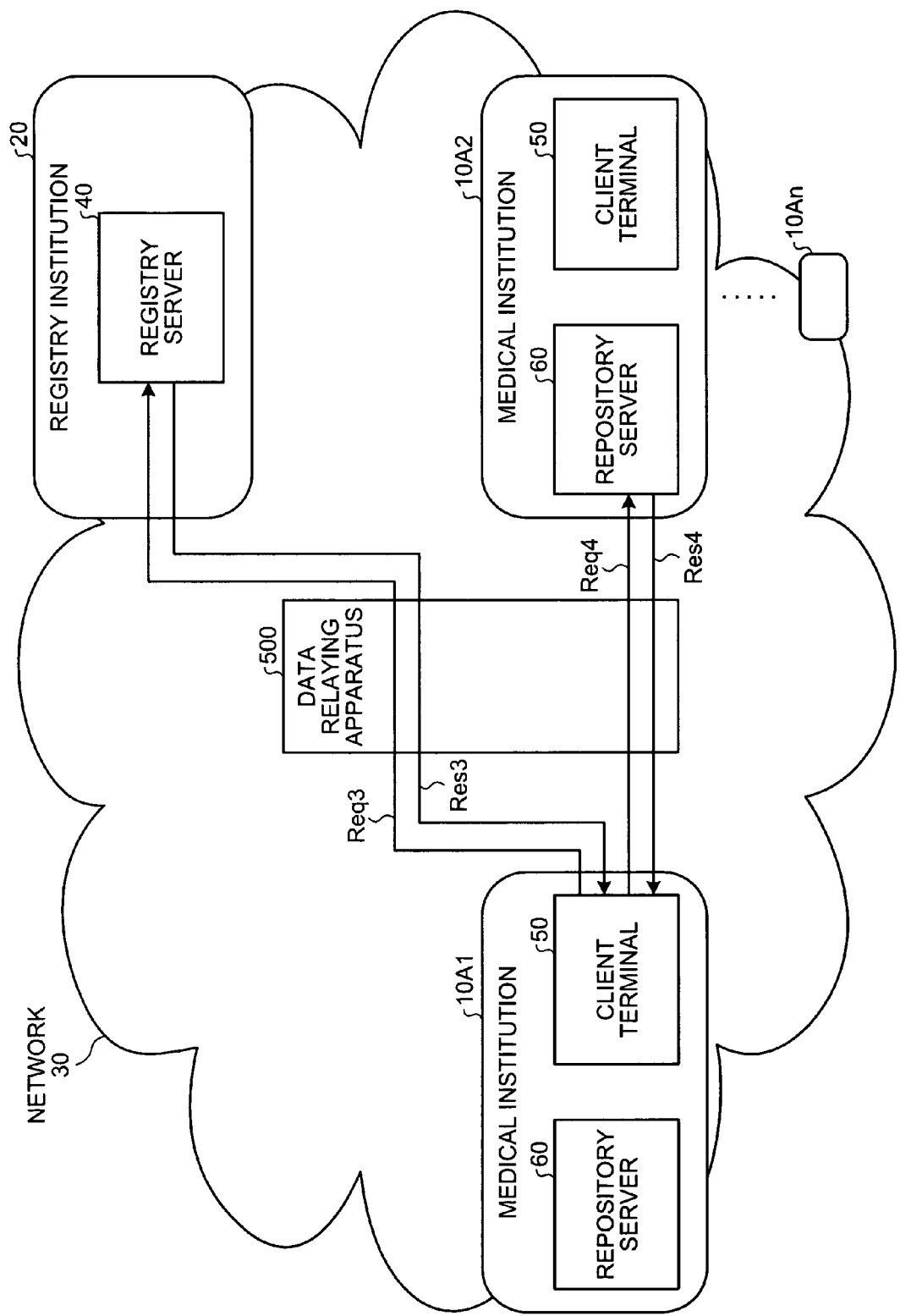
FIG. 10 is an explanatory view of a schematic of a medical network disposed with a data relaying apparatus according to a third embodiment.

FIG. 10 is an explanatory view of a schematic of a medical network disposed with a data relaying apparatus according to the third embodiment; computer networks (LAN and WAN) are established in each institution of the medical institutions 10A1 to 10An and the registry institution 20; and the institutions are communicably connected to each other through the network 30 (public telephone network and Internet) as in the first and second embodiments.

When the registry server 40, the client terminal 50, and the repository server 60 transmit data in the third embodiment, the data are always transmitted through transmission paths going through the data relaying apparatus 500 on the network 30.

This may be implemented by specifying the address of the data relaying apparatus 500 on the network 30 in the proxy setting of the client terminal 50, for example.

As a result, when the client terminal 50 transmits a content retrieval request to the registry server 40 in accordance with user's operation, the content retrieval request is transmitted to the registry server 40 via the data relaying apparatus 500 (Req3).

Similarly, a content retrieval result (Res3) transmitted from the registry server 40, a content acquisition request transmitted (Req4) from the client terminal 50, and contents (Res4) transmitted from the repository server 60 all go through the data relaying apparatus 500 (Res4). The data relaying apparatus 500 corresponds to a data relaying apparatus according to the third embodiment.

Figure 11:
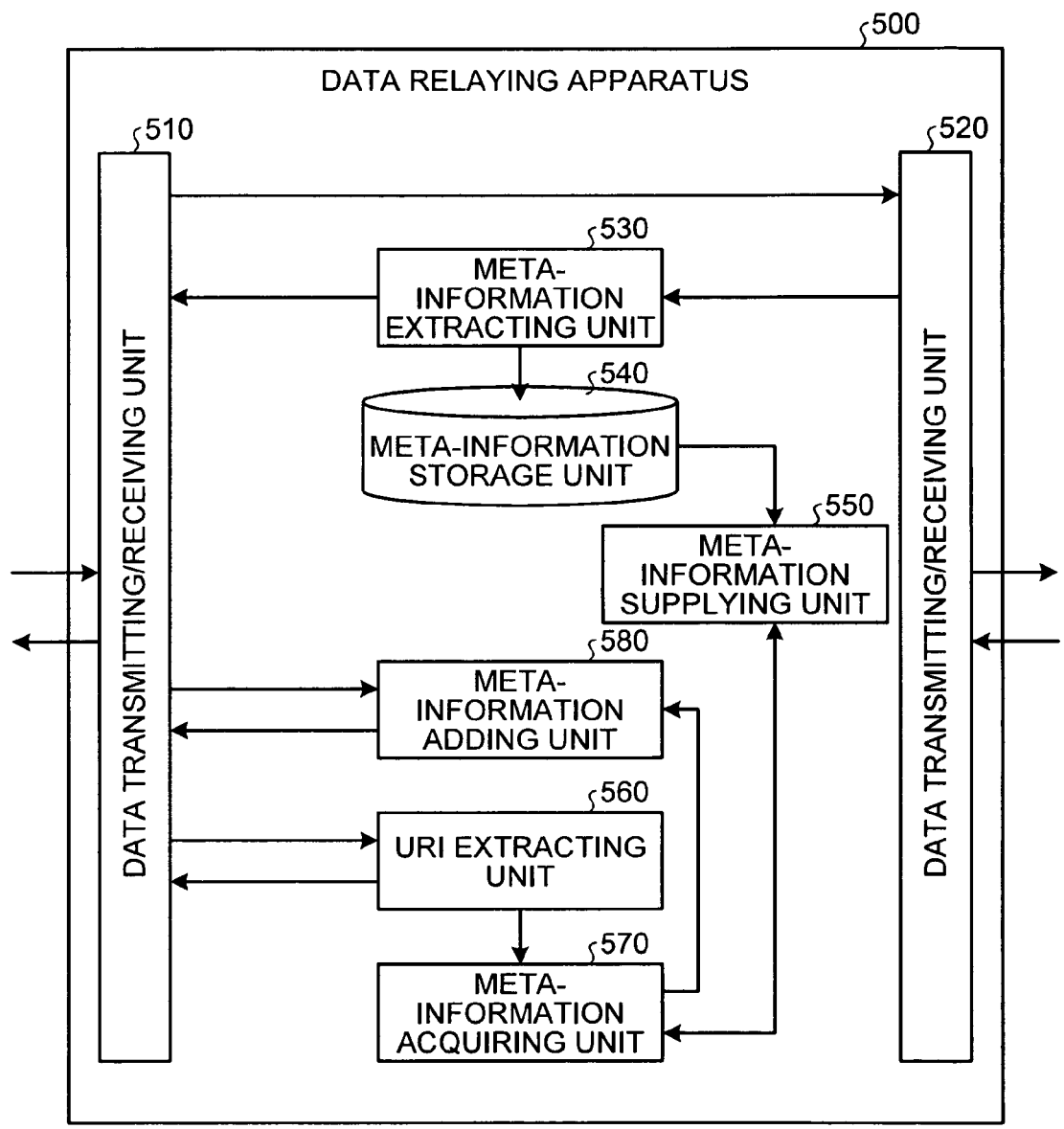
FIG. 11 is a block diagram of a schematic configuration of a data relaying apparatus 500.

A schematic configuration of the data relaying apparatus 500 will be explained with reference to FIG. 11. As shown in FIG. 11, the data relaying apparatus 500 includes data transmitting/receiving units 510 to 520, a meta-information extracting unit 530, a meta-information storage unit 540, a meta-information supplying unit 550, a URI extracting unit 560, a meta-information acquiring unit 570, and a meta-information adding unit 580.

The data transmitting/receiving unit 510 executes transmission/reception processes of data for the medical institutions 10A1 to 10An. The data transmitting/receiving unit 520 executes transmission/reception processes of data for the registry server 40. The data transmitting/receiving unit 510 determines a type of a received message and determines an output destination depending on the determination result.

The meta-information extracting unit 530 extracts meta-information from the content retrieval result transmitted from the registry server 40 to the client terminals 50 and registers and correlates the meta-information with URI information into the meta-information storage unit 540.

Specifically, the meta-information extracting unit 530 receives the content retrieval result from the data transmitting/receiving unit 520 and extracts meta-information from the content retrieval result.

The meta-information extracting unit 530 registers and correlates the extracted meta-information with the URI information included in the meta-information into the meta-information storage unit 540 and outputs the content retrieval result to the data transmitting/receiving unit 510.

The meta-information storage unit 540 accepts the registration to have the meta-information stored thereon. A specific example is as shown in FIG. 4 and will not be explained.

The meta-information supplying unit 550 receives the URI information from the meta-information acquiring unit 570 explained later, acquires meta-information correlated with the URI information from the meta-information storage unit 540, and outputs the meta-information to the meta-information acquiring unit 570.

When receiving a content acquisition request transmitted to the repository server 60 from the client terminal 50, the URI extracting unit 560 extracts the URI information from the content acquisition request.

Specifically, the URI extracting unit 560 receives the content acquisition request from the data transmitting/receiving unit 510, extracts the URI information, outputs the URI information to the meta-information acquiring unit 570, and outputs the content acquisition request to the data transmitting/receiving unit 510.

The meta-information acquiring unit 570 acquires meta-information correlated with the URI information extracted by the URI extracting unit 560 from the meta-information storage unit 540.

Specifically, the meta-information acquiring unit 570 receives the URI information from the URI extracting unit 560 and outputs the URI information to the meta-information supplying unit 550. Since the meta-information supplying unit 550 returns meta-information correlated with the URI information, the meta-information acquiring unit 570 outputs the meta-information to the meta-information adding unit 580.

When relaying the contents transmitted by the repository server 60 to the client terminal 50, the meta-information adding unit 580 adds the meta-information acquired by the meta-information acquiring unit 570 to the contents and relays the contents to the client terminal 50.

Specifically, the meta-information adding unit 580 receives the meta-information from the meta-information acquiring unit 570. The meta-information adding unit 580 subsequently receives contents from the data transmitting/receiving unit 510, adds the meta-information to the contents, and outputs the contents to the data transmitting/receiving unit 510.

Figure 12:
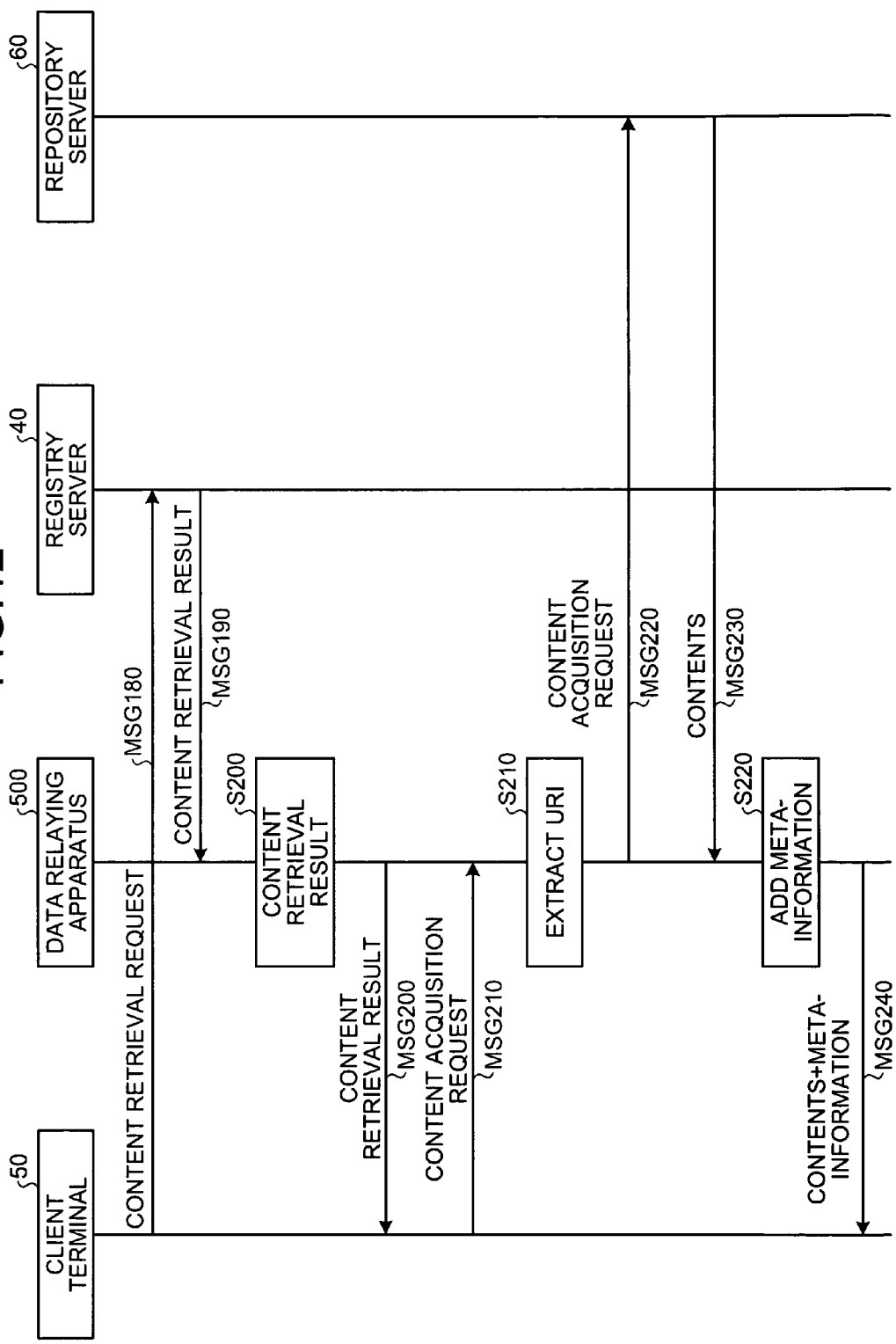
FIG. 12 is a sequence view of a schematic of a process in apparatuses of the third embodiment.

A process flow of the apparatuses will then be explained with reference to FIG. 12. The client terminal 50 first transmits a content retrieval request to the registry server 40 (MSG180).

The registry server 40 receives the content retrieval request through the data relaying apparatus 500 and transmits a content retrieval result to the client terminal 50 (MSG190).

When relaying the content retrieval result to the client terminal 50 (MSG200), the data relaying apparatus 500 extracts, retains, and correlates meta-information with the URI information (Step S200).

The client terminal 50 receives the content retrieval result through the data relaying apparatus 500 and transmits a content acquisition request to the repository server 60 (MSG210).

The data relaying apparatus 500 extracts the URI information from the content acquisition request (Step S210) and acquires the meta-information correlated to the URI information from the meta-information storage unit 540.

The data relaying apparatus 500 relays the content acquisition request to the repository server 60 (MSG220).

The repository server 60 receives the content acquisition request through the data relaying apparatus 500 and transmits contents to the client terminal 50 (MSG230).

The data relaying apparatus 500 receives the contents from the repository server 60, adds the meta-information received earlier (Step S220), and relays the contents to the client terminal 50 (MSG240).

Figure 13:
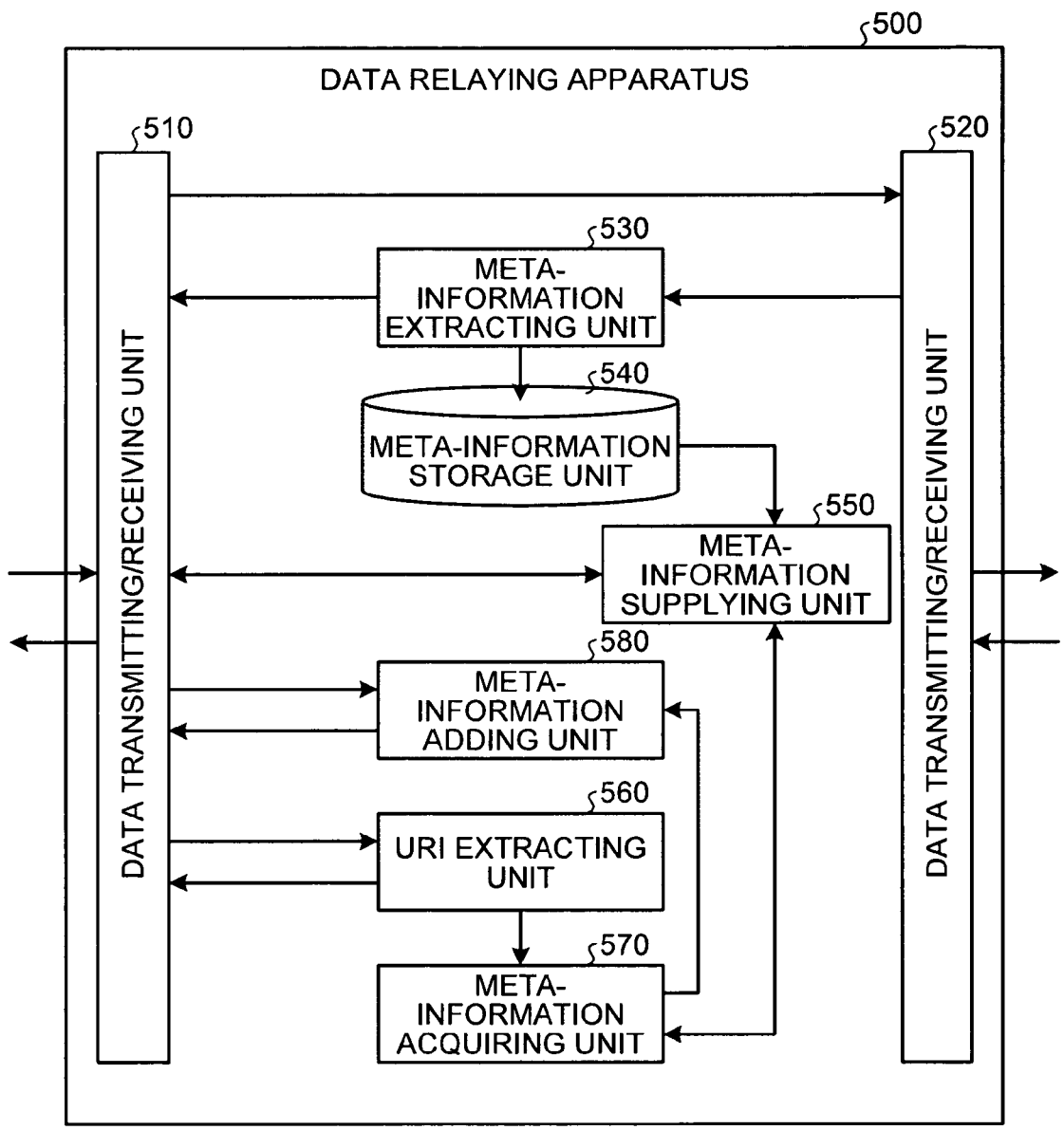
FIG. 13 is an explanatory view of a variation of the data relaying apparatus according to the third embodiment.

If the meta-information supplying unit 550 and the meta-information acquiring unit 570 are capable of communicating with the outside through the data transmitting/receiving unit 510 as shown in FIG. 13, the data relaying apparatus 500 may be disposed on the preceding stage of the registry server 40 and the preceding stage of the repository server 60 as in the first and second embodiments.

In this case, for example, the meta-information supplying unit 550 of the data relaying apparatus 500 disposed on the preceding stage of the registry server 40 receives URI information from the data transmitting/receiving unit 510 and outputs the meta-information acquired from the meta-information storage unit 540 to the data transmitting/receiving unit 510.

The meta-information acquiring unit 570 of the data relaying apparatus 500 disposed on the preceding stage of the repository server 60 outputs URI information to the data transmitting/receiving unit 510 to acquire meta-information from the data relaying apparatus 500 disposed on the preceding stage of the registry server 40.

Figure 14:
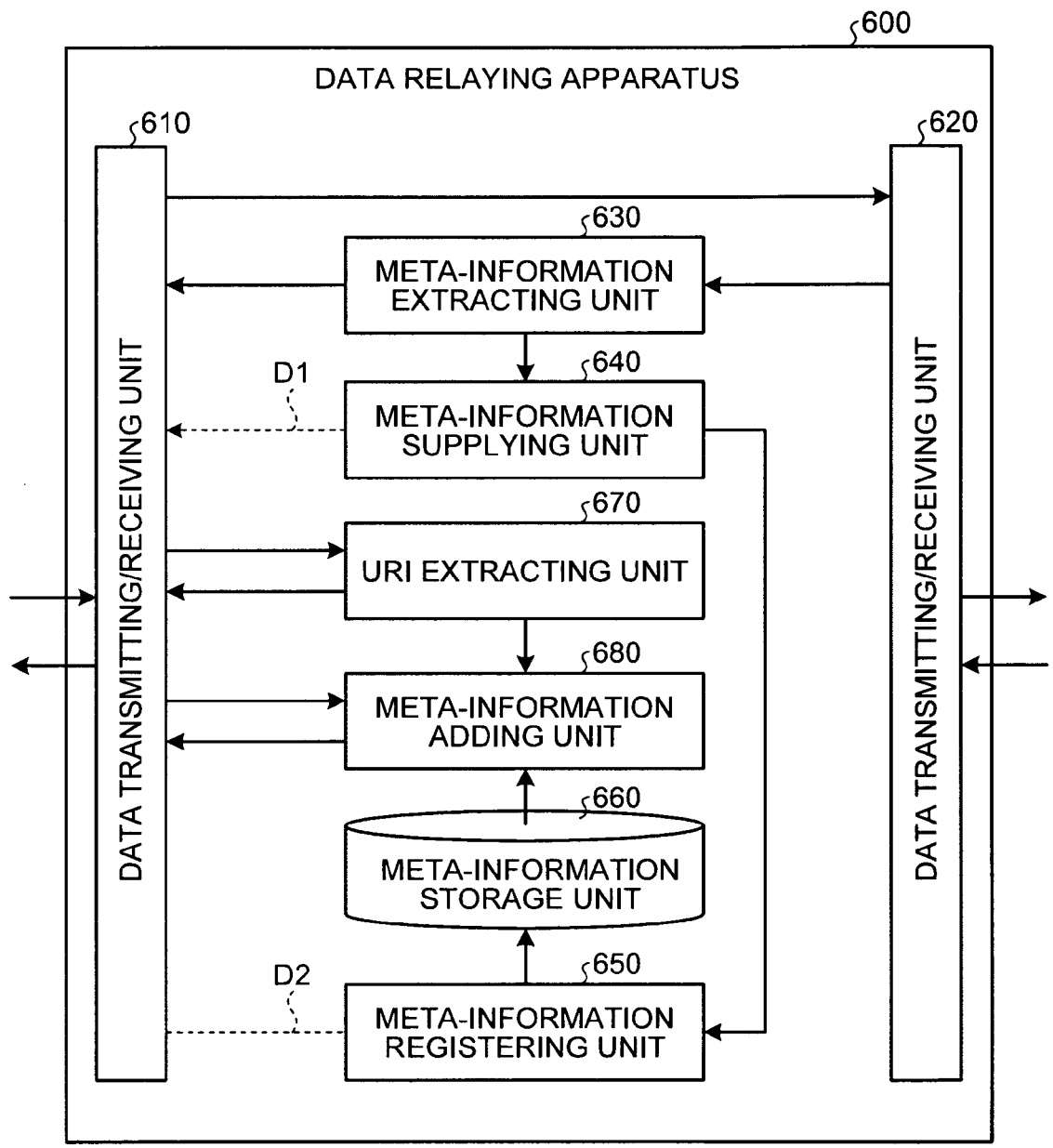
FIG. 14 is an explanatory view of a variation of the data relaying apparatus according to the third embodiment.
Figure 15:
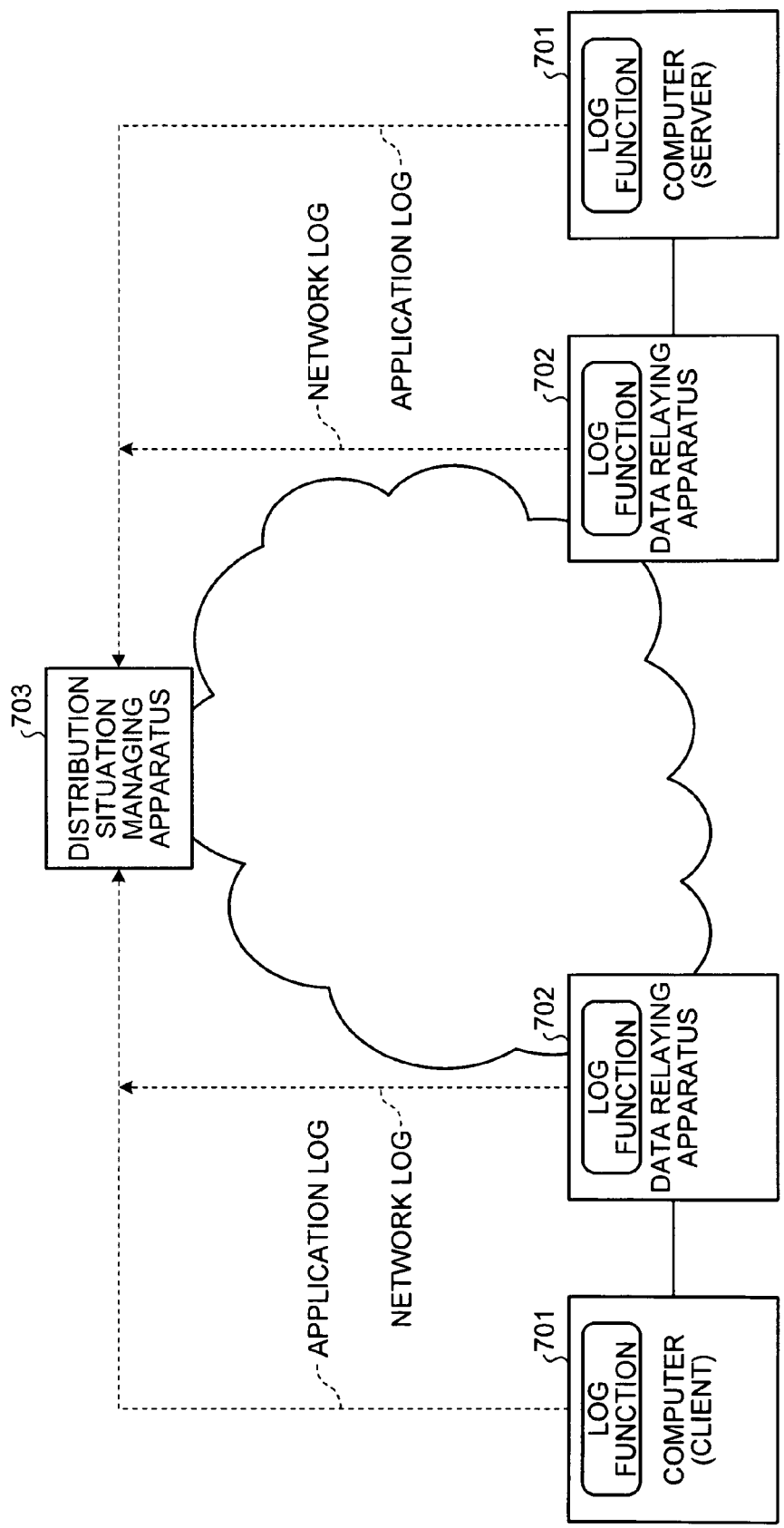
FIG. 15 is an explanatory view of a first conventional technology.
Figure 16:
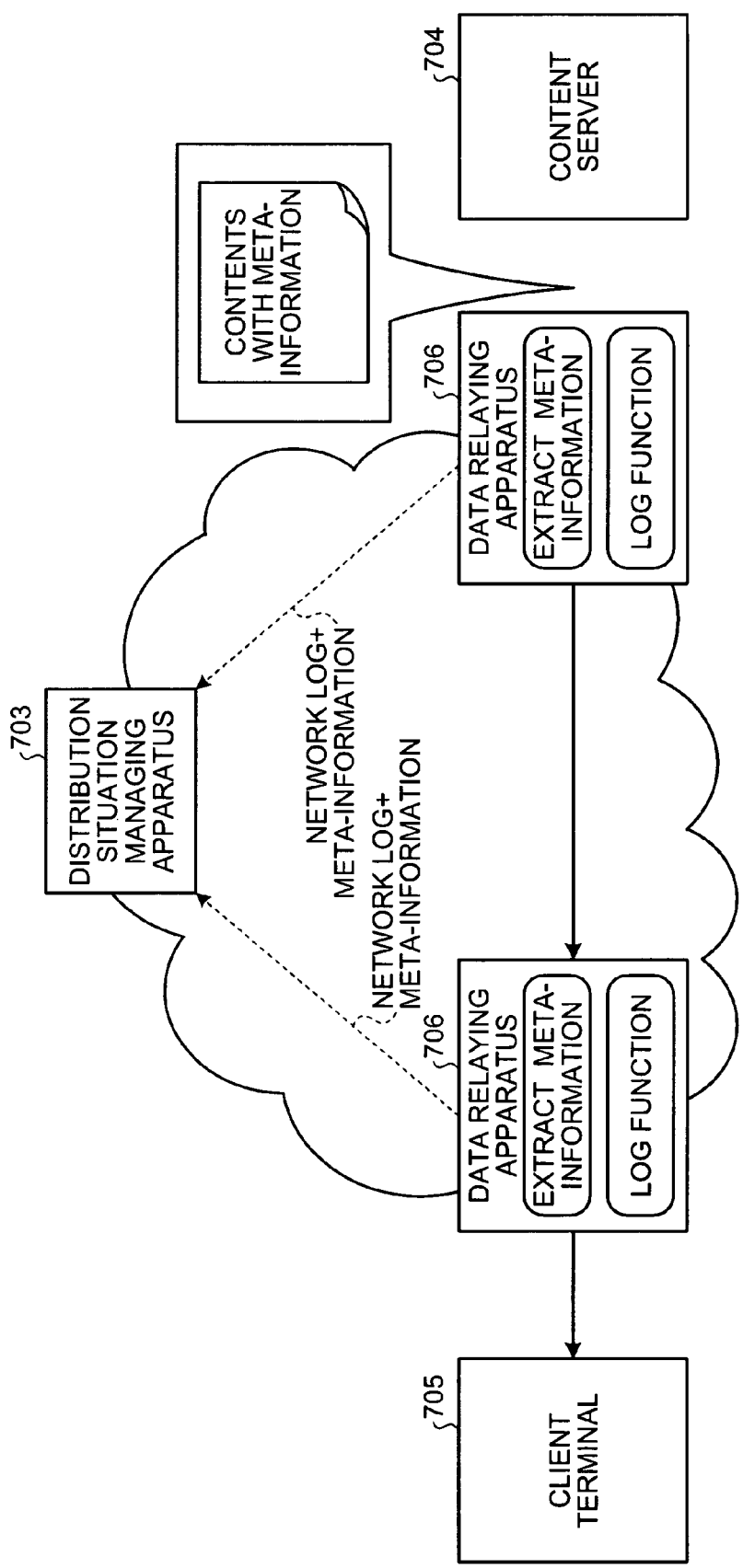
FIG. 16 is an explanatory view of a second conventional technology.
Figure 17:
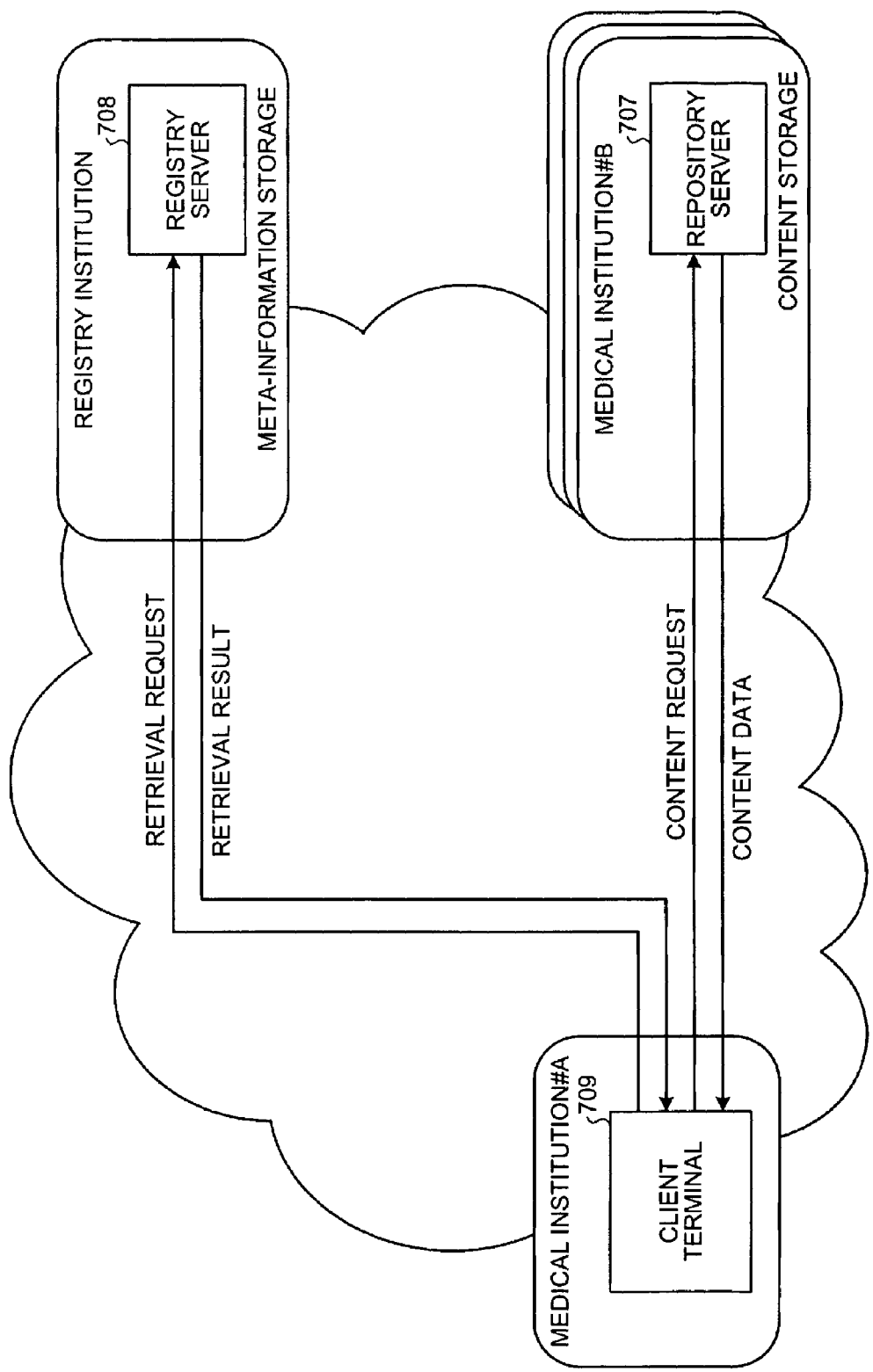
FIG. 17 is an explanatory view of XDS.

A data relaying apparatus according to the third embodiment may have a configuration shown in FIG. 14. As shown in FIG. 14, a data relaying apparatus 600 includes in one apparatus the constituent elements of the data relaying apparatus 300 and the data relaying apparatus 400 explained in the second embodiment.

Referring to FIG. 14, data transmitting/receiving units 610 to 620 correspond to the data transmitting/receiving units 310 to 320; a meta-information extracting unit 630 corresponds to the meta-information extracting unit 330; a meta-information supplying unit 640 corresponds to the meta-information supplying unit 340; a meta-information registering unit 650 corresponds to the meta-information registering unit 430; a meta-information storage unit 660 corresponds to the meta-information storage unit 440; a URI extracting unit 670 corresponds to the URI extracting unit 450; and a meta-information adding unit 680 corresponds to the meta-information adding unit 460.

Although the meta-information supplying unit 340 supplies meta-information to the outside, the meta-information supplying unit 640 supplies meta-information to the meta-information registering unit 650 since the destination is within the apparatus in the case of the data relaying apparatus 600.

As shown in FIG. 14, if the meta-information supplying unit 640 and the meta-information registering unit 650 are capable of communicating to the outside through a data transmitting/receiving unit 610 (see dot-line arrows), the data relaying apparatus 600 may be disposed on the preceding stage of the registry server 40 and the preceding stage of the repository server 60 as in the first and second embodiments.

In this case, the meta-information supplying unit 640 of the data relaying apparatus 600 disposed on the preceding stage of the registry server 40 supplies meta-information to another data relaying apparatus 600 through the data transmitting/receiving unit 610 (D1). The meta-information registering unit 650 of the data relaying apparatus 600 disposed on the preceding stage of the repository server 60 receives meta-information through the data transmitting/receiving unit 610 (D2).

Lastly, the constituent elements show in FIGS. 2, 5, 7, 8, 11, 13, and 14 are functionally conceptual and may not necessarily physically be configured as shown.

A specific form of the distribution/integration of the apparatuses is not limited to the form shown and a whole or part thereof may functionally or physically be distributed/integrated in any scale depending on various loads and usage situations, for example, by dividing the meta-information extracting unit 130 into a meta-information extracting unit and a meta-information registering unit.

The processing functions executed in the apparatuses may wholly or partially be implemented by a CPU and a program analyzed and executed by the CPU or implemented by hardware through wired logic.

The apparatus disclosed herein extracts meta-information from a content retrieval result and retains and correlates the meta-information with a unique identifier included in the meta-information. If contents are subsequently relayed to a client terminal, the contents are relayed with the meta-information of the contents added. Therefore, when this apparatus relays contents, the control of distribution situations of contents may strictly be performed by recording meta-information and communication information related to the relay.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A data relaying apparatus disposed on a network with contents and meta-information managed separately in different servers, the data relaying apparatus comprising:
a location information extracting unit that extracts location information uniquely defining a location of contents from a content acquisition request, the content acquisition request being transmitted from a client terminal to a repository server retaining the contents;
a meta-information acquiring unit that transmits a meta-information acquisition request to a data relaying apparatus cooperating with a registry server managing the meta-information with the use of the location information extracted by the location information extracting unit to acquire meta-information;
a content transmitting unit that receives contents to add the meta-information acquired by the meta-information acquiring unit to the contents, the contents being transmitted by the repository server accepting the content acquisition request to the client terminal transmitting the content acquisition request, the content transmitting unit relaying the contents to the client terminal; and
a log writing unit that writes the meta-information added to the contents and communication information related to relaying when the content transmitting unit relays the contents, the communication information including an access time.

2. The data relaying apparatus according to claim 1, further comprising a log transmitting unit that transmits information written by the log writing unit to a predetermined transmission destination.

3. A data relaying apparatus disposed on a network with contents and meta-information managed separately in different servers, the data relaying apparatus comprising:
a meta-information extracting unit that extracts meta-information from a content retrieval result, the content retrieval result being transmitted to a client terminal from a registry server accepting a content retrieval request from the client terminal, the registry server managing the meta-information;
a meta-information transmitting unit that transmits the meta-information extracted by the meta-information extracting unit to a destination determined by location information included in the meta-information, the location information uniquely defining a location of contents; and
a log writing unit that writes the meta-information added to the contents and communication information related to relaying when the content retrieval result is transmitted, the communication information including an access time.

4. A data relaying apparatus disposed on a network with contents and meta-information managed separately in different servers, the data relaying apparatus comprising:
a meta-information registering unit that registers meta-information into a meta-information storage unit in correlation with location information included in the meta-information, the location information uniquely defining a location of contents, the meta-information being received from a data relaying apparatus cooperating with a registry server managing the meta-information;
a location information extracting unit that extracts the location information from the content acquisition request, the content acquisition request being transmitted from a client terminal to a repository server retaining the contents;
a meta-information acquiring unit that acquires meta-information correlated with the location information extracted by the location information extracting unit from the meta-information storage unit;
a content relaying unit that receives contents to add the meta-information acquired by the meta-information acquiring unit to the contents, the contents being transmitted by the repository server accepting the content acquisition request to the client terminal transmitting the content acquisition request, the content relaying unit relaying the contents to the client terminal; and
a log writing unit that writes the meta-information added to the contents and communication information related to relaying when the content relaying unit relays the contents, the communication information including an access time.

5. The data relaying apparatus according to claim 4, further comprising a log transmitting unit that transmits information written by the log writing unit to a predetermined transmission destination.

6. A data relaying apparatus disposed on a network with contents and meta-information managed separately in different servers, the data relaying apparatus comprising:
a meta-information extracting unit that extracts meta-information from a content retrieval result, the content retrieval result being transmitted to a client terminal from a registry server accepting a content retrieval request from the client terminal, the registry server centrally managing the meta-information;
a meta-information registering unit that registers the meta-information extracted by the meta-information extracting unit into a meta-information storage unit in correlation with location information included in the meta-information, the location information uniquely defining a location of contents;

a location information extracting unit that receives a content acquisition request to extract the location information from the content acquisition request, the content acquisition request being transmitted to a repository server retaining the contents;

a meta information acquiring unit that acquires meta-information correlated with the location information extracted by the location information extracting unit from the meta-information storage unit;

a content transmitting unit that receives contents to add the meta-information acquired by the meta-information acquiring unit to the contents, the contents being transmitted by the repository server accepting the content acquisition request to the client terminal transmitting the content acquisition request, the content transmitting unit relaying the contents to the client terminal; and a log writing unit that writes the meta-information added to the contents and communication information related to relaying when the content transmitting unit relays the contents, the communication information including an access time.

7. The data relaying apparatus according to claim 6, further comprising a meta-information transmitting unit that externally receives a meta-information acquisition request with the location information specified to retrieve meta-information correlated with the location information from the meta-information storage unit, the meta-information transmitting unit transmitting the meta-information acquired as a result of the retrieval to a request source, wherein the meta-information acquiring unit transmits a meta-information acquisition request to a data relaying apparatus cooperating with the registry server with the use of the location information extracted by the location information extracting unit to acquire meta-information.

8. The data relaying apparatus according to claim 6, further comprising a meta-information transmitting unit that transmits the meta-information extracted by the meta-information extracting unit to a destination determined by location information included in the meta-information, the location information uniquely defining a location of contents, wherein the meta-information registering unit receives meta-information from a data relaying apparatus cooperating with the registry server to register the meta-information into the meta-information storage unit in correlation with the location information.

9. The data relaying apparatus according to claim 6, further comprising a log transmitting unit that transmits information written by the log writing unit to a predetermined transmission destination.

10. A method for relaying data in a network with contents and meta-information managed separately in different servers, the method comprising:

extracting location information uniquely defining a location of contents from a received content acquisition request transmitted from a client terminal to a repository server retaining the contents;

acquiring meta-information by transmitting a meta-information acquisition request to a data relaying apparatus cooperating with a registry server managing the meta-information with the use of the extracted location information; and adding the acquired meta-information to contents, the contents being transmitted from the repository server accepting the content acquisition request to the client terminal transmitting the content acquisition request;

relaying the contents with the meta-information to the client terminal; and writing the meta-information added to the contents and communication information related to relaying when the relaying relays the contents, the communication information including an access time.

11. A method for relaying data in a network with contents and meta-information managed separately in different servers, the method comprising:

extracting meta-information from a received content retrieval result transmitted to a client terminal from a registry server accepting a content retrieval request from the client terminal, the registry server managing the meta-information;

transmitting the extracted meta-information to a destination determined by location information included in the meta-information, the location information uniquely defining a location of contents; and writing the meta-information added to the contents and communication information related to relaying when the content retrieval result is transmitted, the communication information including an access time.

12. A method for relaying data in a network with contents and meta-information managed separately in different servers, the method comprising:

registering meta-information into a storage unit in correlation with location information included in the meta-information, the meta-information being received from a data relaying apparatus cooperating with a registry server managing the meta-information, the location information uniquely defining a location of contents;

extracting the location information from the content acquisition request, the content acquisition request being transmitted from a client terminal to a repository server retaining the contents;

acquiring meta-information correlated with the extracted location information from the storage unit;

adding the acquired meta-information to contents, the contents being transmitted from the repository server accepting the content acquisition request to the client terminal transmitting the content acquisition request relaying the contents with the meta-information to the client terminal; and writing the meta-information added to the contents and communication information related to relaying when the relaying relays the contents, the communication information including an access time.

13. A method for relaying data in a network with contents and meta-information managed separately in different servers, the method comprising:

extracting meta-information from a content retrieval result, the content retrieval result being transmitted to a client terminal from a registry server accepting a content retrieval request from the client terminal, the registry server centrally managing the meta-information;

registering the extracted meta-information into a storage unit in correlation with location information included in the meta-information, the location information uniquely defining a location of contents;

extracting the location information from a content acquisition request transmitted to a repository server retaining the contents;

acquiring meta-information correlated with the extracted location information from the storage unit;

adding the acquired meta-information to the contents, the contents being transmitted from the repository server accepting the content acquisition request to the client terminal transmitting the content acquisition request;

relaying the contents with the meta-information to the client terminal; and writing the meta-information added to the contents and communication information related to relaying when the relaying relays the contents, the communication information including an access time.

14. A non-transitory computer-readable recording medium that stores therein a computer program that causes a computer to relay data in a network with contents and meta-information managed separately in different servers, the computer program causing the computer to execute:

extracting location information uniquely defining a location of contents from a received content acquisition request transmitted from a client terminal to a repository server retaining the contents;

acquiring meta-information by transmitting a meta-information acquisition request to a data relaying apparatus cooperating with a registry server managing the meta-information with the use of the extracted location information;

adding the acquired meta-information to contents, the contents being transmitted from the repository server accepting the content acquisition request to the client terminal transmitting the content acquisition request;

relaying the contents with the meta-information to the client terminal;

writing the meta-information added to the contents and communication information related to relaying when the relaying relays the contents, the communication information including an access time.

15. A non-transitory computer-readable recording medium that stores therein a computer program that causes a computer to relay data in a network with contents and meta-information managed separately in different servers, the computer program causing the computer to execute:

extracting meta-information from a received content retrieval result transmitted to a client terminal from a registry server accepting a content retrieval request from the client terminal, the registry server managing the meta-information;

transmitting the extracted meta-information to a destination determined by location information included in the meta-information, the location information uniquely defining a location of contents; and writing the meta-information added to the contents and communication information related to relaying when the content retrieval result is transmitted, the communication information including an access time.

16. A non-transitory computer-readable recording medium that stores therein a computer program that causes a computer to relay data in a network with contents and meta-information managed separately in different servers, the computer program causing the computer to execute:

registering meta-information into a storage unit in correlation with location information included in the meta-information, the meta-information being received from a data relaying apparatus cooperating with a registry server managing the meta-information, the location information uniquely defining a location of contents;

extracting the location information from the content acquisition request, the content acquisition request being transmitted from a client terminal to a repository server retaining the contents;

acquiring meta-information correlated with the extracted location information from the storage unit;

adding the acquired meta-information to contents, the contents being transmitted from the repository server accepting the content acquisition request to the client terminal transmitting the content acquisition request;

relaying the contents with the meta-information to the client terminal; and writing the meta-information added to the contents and communication information related to relaying when the relaying relays the contents, the communication information including an access time.

17. A non-transitory computer-readable recording medium that stores therein a computer program that causes a computer to relay data in a network with contents and meta-information managed separately in different servers, the computer program causing the computer to execute:

extracting meta-information from a content retrieval result, the content retrieval result being transmitted to a client terminal from a registry server accepting a content retrieval request from the client terminal, the registry server centrally managing the meta-information;

registering the extracted meta-information into a storage unit in correlation with location information included in the meta-information, the location information uniquely defining a location of contents;

extracting the location information from a content acquisition request transmitted to a repository server retaining the contents;

acquiring meta-information correlated with the extracted location information from the storage unit;

adding the acquired meta-information to the contents, the contents being transmitted from the repository server accepting the content acquisition request to the client terminal transmitting the content acquisition request;

relaying the contents with the meta-information to the client terminal; and writing the meta-information added to the contents and communication information related to relaying when the relaying relays the contents, the communication information including an access time.

* * * * *